United States Patent
Ito

(10) Patent No.: US 6,589,365 B2
(45) Date of Patent: Jul. 8, 2003

(54) METHOD OF FORMING AN OXIDE FILM ON A METALLIC MEMBER

(75) Inventor: Michio Ito, Nagano (JP)

(73) Assignee: Matsumoto Dental University, Nagano (JP)

(*) Notice: Subject to any disclaimer, the term of this patent is extended or adjusted under 35 U.S.C. 154(b) by 0 days.

(21) Appl. No.: 10/260,572

(22) Filed: Oct. 1, 2002

(65) Prior Publication Data

US 2003/0064170 A1 Apr. 3, 2003

(30) Foreign Application Priority Data

Oct. 1, 2001 (JP) ........................................ 2001-305347

(51) Int. Cl.⁷ ................................................ C23C 8/00
(52) U.S. Cl. ................... 148/241; 148/243; 148/277; 148/280; 148/284; 427/2.26; 427/2.27; 427/301
(58) Field of Search ............................... 148/241, 243, 148/277, 280, 284; 427/2.26, 2.27, 301

(56) References Cited

U.S. PATENT DOCUMENTS 4,366,125 A * 12/1982 Kodera et al. ............... 422/295
6,277,213 B1 * 8/2001 Schenker ..................... 148/243

FOREIGN PATENT DOCUMENTS

| EP | 1067092 A1 | 1/2001 | |
| EP | 1096039 A2 * | 5/2001 | .......... C23C/22/68 |
| JP | 02 040322 A | 2/1990 | |

* cited by examiner

Primary Examiner—John Sheehan
Assistant Examiner—Andrew L. Oltmans
(74) Attorney, Agent, or Firm—Foley & Lardner

(57) ABSTRACT

A hydrogen peroxide solution is applied onto the surface of a metallic member to oxidize the metallic member and to form the oxide film. At this time, a light beam is irradiated towards the metallic member through the hydrogen peroxide solution to promote oxidization of the metallic member. The light beam is one of a visible ray, a laser beam, and an ultraviolet ray.

18 Claims, 6 Drawing Sheets

METHOD OF FORMING AN OXIDE FILM ON A METALLIC MEMBER

BACKGROUND OF THE INVENTION

This invention relates to a method of forming an oxide film on a metallic member for a dental treatment and, in particular, to a method of forming an oxide film to adhere a metallic member to an object by the use of an adhesive.

Traditionally, a metallic member is often fixed on a dental treatment through an adhesive to a fixing site, such as an affected part of a patient's tooth. As a metallic material in a dental field, known is an orthodontic bracket, a crown or a bridge as a prosthetic material, or an inlay for conservative restoration.

As the adhesive used in dental treatment, a dental cement is known. As an existing adhering technique, the following methods are adopted in order to improve the adhesive strength between the metallic member and the dental cement.

As a first adhering method, the surface of the metallic member is sandblasted. In this state, the metallic member is placed on the affected part of the patient as the fixing site through the dental cement and fixed by the dental cement.

As a second adhering method, the metallic member to be adhered is heated in an electric furnace to be oxidized. Thereafter, the metallic member is adhered to the fixing site. When the metallic member is oxidized and is adhered to the fixing site through the dental cement, an oxide film is helpful to firmly secure the metallic member to the fixing site. This is because the adhesive such as the dental cement has an improved wettability due to the presence of the oxide film.

Taking the above into consideration, an oxide film has been usually formed on a whole surface of the metallic member. Thus, the metallic member with the oxide film is placed onto the affected part of the patient. In this event, the oxide film should be partially removed or polished from the metallic member to obtain a mirror-finished surface before the metallic member is placed onto the affected part of the patient, on account of the fact that the dental cement as the adhesive is partially coated on the metallic member.

On the other hand, an implant used in the dental field may be directly implanted in the affected part of the patient to be bonded to a living bone after the implant is heated and oxidized in the electric furnace. In this case, the implant acts as the metallic member while the living bone, the fixing site.

At any rate, a very long time is required to polish the oxide film on the metallic member before placement of the metallic member onto the fixing site. In addition, the metallic member may be deteriorated in quality because it is heated in the electric furnace in order to oxidize the surface.

SUMMARY OF THE INVENTION

It is an object of this invention to provide a method of forming an oxide film on a metallic member, which is capable of avoiding deterioration of the metallic member that might occur on forming the oxide film at high temperature.

It is another object of this invention to provide a method of the type described, which dispenses with long time polishing before placement of the metallic member onto the fixing site.

It is still another object of this invention to provide a method of the type described, which is capable of improving reliability and strength in adhesion.

According to this invention, there is provided a method of forming an oxide film a metallic member, the method comprising the steps of (1) selectively applying a hydrogen peroxide solution onto a partial surface of the metallic member and (2) irradiating a light beam onto the partial surface through the hydrogen peroxide solution to selectively and locally form the oxide film onto the metallic member. The light beam is selected from a group consisting of a visible ray, a laser beam, and an ultraviolet ray.

The metallic member may be made of a material selected from a group comprising a cobalt-chromium alloy, a nickel-chromium alloy, a stainless steel, pure titanium, a titanium alloy, a platinum gold alloy, a gold-silver-palladium alloy, a silver alloy, and a gold alloy.

The metallic member may be an implant to be implanted in a living bone.

DESCRIPTION OF THE PREFERRED EMBODIMENT

Now, description will be made of a method of forming an oxide film according to one embodiment of this invention.

Figure 1:
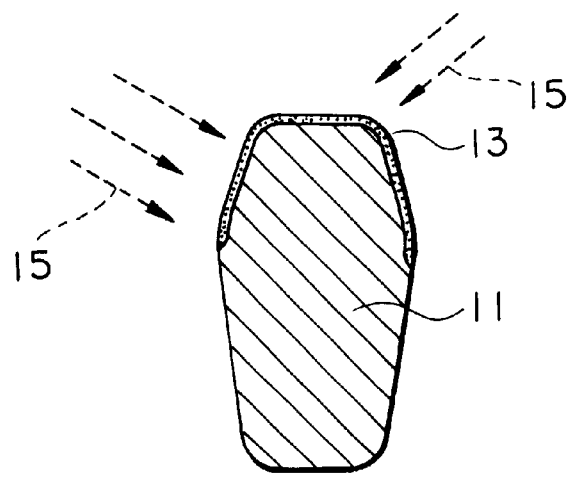
FIG. 1 is a sectional view for describing a method of forming an oxide film according to a preferred embodiment of this invention.
Figure 2:
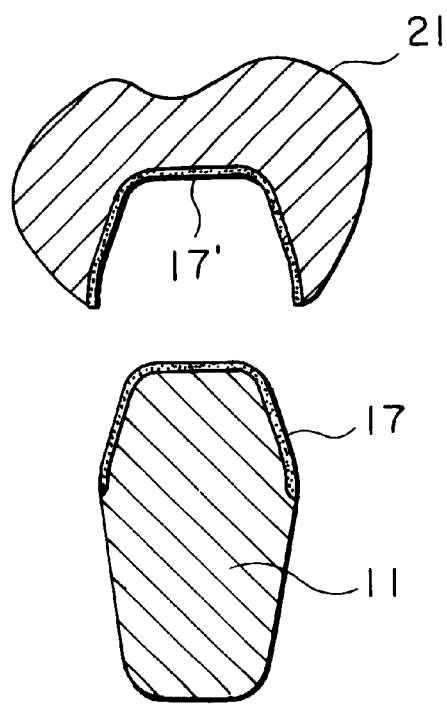
FIG. 2 is a sectional view showing a metallic member in FIG. 1 after a oxide film is formed thereon and before the metallic member is adhered to an object.

Referring to FIGS. 1 and 2, a metallic member 11 is an implant used in a dental field while an object 21 (FIG. 2) to be adhered and fixed to the metallic member 11 is a metallic crown. Thus, in the illustrated example, the object 21 also serves as a metallic member similar to the metallic member 11.

At first referring to FIG. 1, a hydrogen peroxide ($H_2O_2$) solution 13 is selectively or locally applied onto the metallic member 11. The hydrogen peroxide solution 13 is kept at a temperature between 10° C. and 80° C. Under the circumstances, a light beam is locally irradiated onto a local surface of the metallic member 11 through the hydrogen peroxide solution 13 to form an oxide film 17 as illustrated in FIG. 2. Thereafter, if the hydrogen peroxide solution 13 is left on the surface of the metallic member 11, the hydrogen peroxide solution 13 is removed. As a consequence, the oxide film 17 is exposed on the surface of the metallic member 11.

Turning back to FIG. 1, after the hydrogen peroxide solution 13 is applied on the metallic member 11, a light beam 15 is irradiated towards the partial surface of the metallic member 11 through the hydrogen peroxide solution 13 to form an oxide film. The light beam 15 may be a visible ray, a laser beam, or an ultraviolet ray. By irradiating the light beam 15 selected from the visible ray, the laser beam, and the ultraviolet ray to the hydrogen peroxide solution 13, the hydrogen peroxide solution 13 is activated to produce hydro radicals on the surface of the metallic member 11 so that the partial surface of the metallic member 11 is quickly oxidized.

In order to apply the hydrogen peroxide solution 13 onto the partial surface of the metallic member 11, various methods may be used. For example, the hydrogen peroxide solution 13 is dropped onto the surface of the metallic member 11. Alternatively, the hydrogen peroxide solution 13 is absorbed in cotton or sponge for wetting the partial surface of the metallic member 11 in contact therewith.

The oxide film 17 is formed on the partial surface of the metallic member 11 when the light beam 15 is irradiated through the hydrogen peroxide solution applied onto the metallic member 11 and then when a time between 30 and 50 seconds lapses.

The metallic member 11 may be made of a material, such as pure titanium (Ti), a titanium alloy, a gold-silver-palladium (Au—Ag—Pd) alloy, a silver (Ag) alloy, a cobalt-chromium (Co—Cr) alloy, a nickel-chromium (Ni—Cr) alloy, a stainless steel, a platinum gold alloy, or a gold (Au) alloy.

On the other hand, the object (crown in the illustrated example) 21 to be fixed to the metallic member 11 is provided with an oxide film 17' formed by a similar oxidization process in a predetermined area to be adhered and fixed to the metallic member 11.

Figure 3:
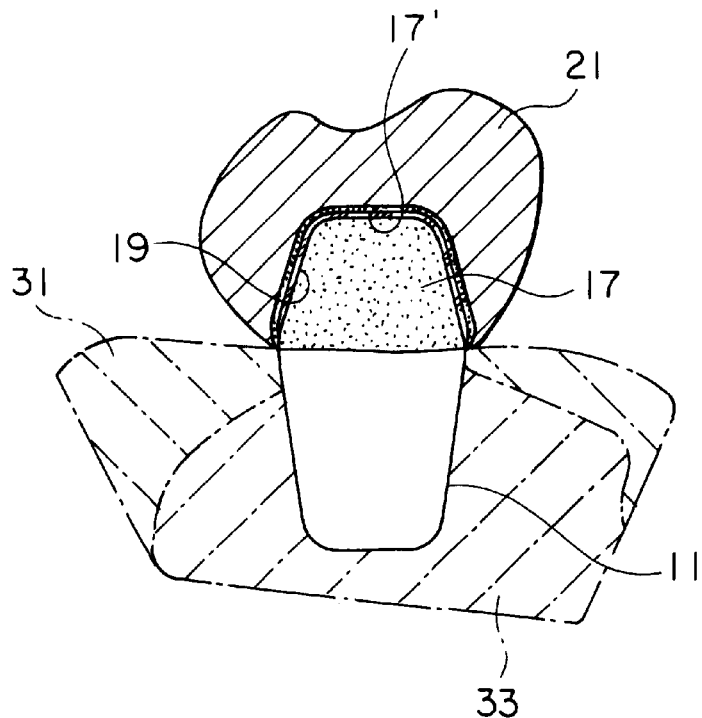
FIG. 3 is a sectional view showing the metallic member in FIG. 2 after it is adhered to the object and fixed in a fixing site.

Referring to FIG. 3, the metallic member 11 with the oxide film 17 formed thereon is adhered to the object 21 by an adhesive. For example, the object 21 to be fixed to an affected part of a patient in a dental field may be an orthodontic bracket, a crown (in the illustrated example) or a bridge as a prosthetic material, or an inlay for conservative restoration, which is prepared by a metal similar to the metallic member 11. The adhesive 19 may be a resin-based adhesive.

Then, the metallic member 11 with the object 21 adhered thereto is implanted in a bone 31 as the affected part of the patient. At this time, a lower part of the metallic member 11 is buried in a bone marrow 33 of the bone 31. The surface of the metallic member 11 and the surface of the predetermined area of the object 21 are provided with the oxide films 17 and 17', respectively, according to the above-mentioned method. These oxide films 17 and 17' are equivalent in quality to those obtained by oxidization in an electric furnace. Therefore, it is possible to avoid deterioration in quality of the metallic member as a result of formation of the oxide film at high temperature. In addition, a long polishing time is not required because the oxide film is formed only onto the partial surface to be adhered to the object 21. By adhering the metallic member 11 in the above-mentioned manner, adhesive strength between the metallic member 11 and the adhesive 19 is improved.

As an experimental example, a titanium plate was used as the metallic member 11 and the oxide film 17 was formed thereon. By the use of a spectrometer, measurement was made of change in the CIE L* a* b* color systems as a color specification system.

Figure 4:
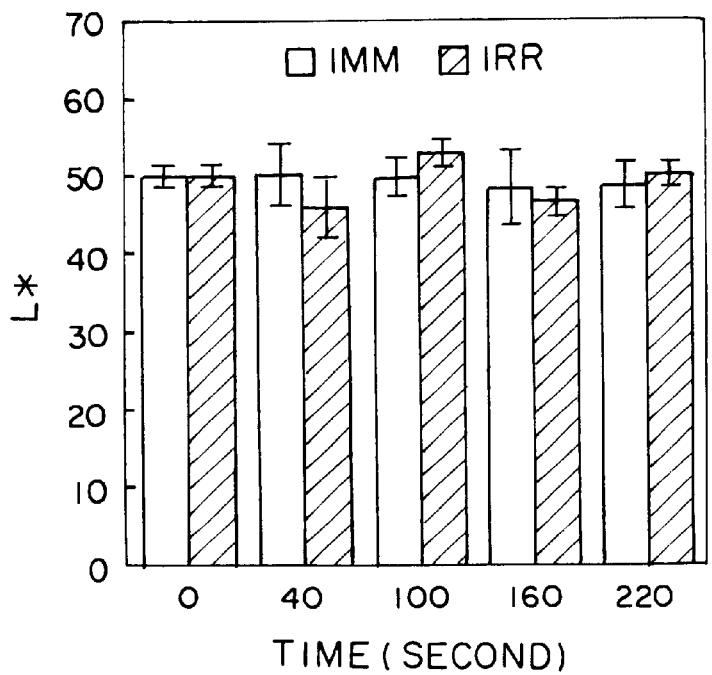
FIG. 4 is a graph showing the relationship between the change in the L* color system of the oxide film illustrated in FIG. 2 and the irradiation time of a visible ray.
Figure 5:
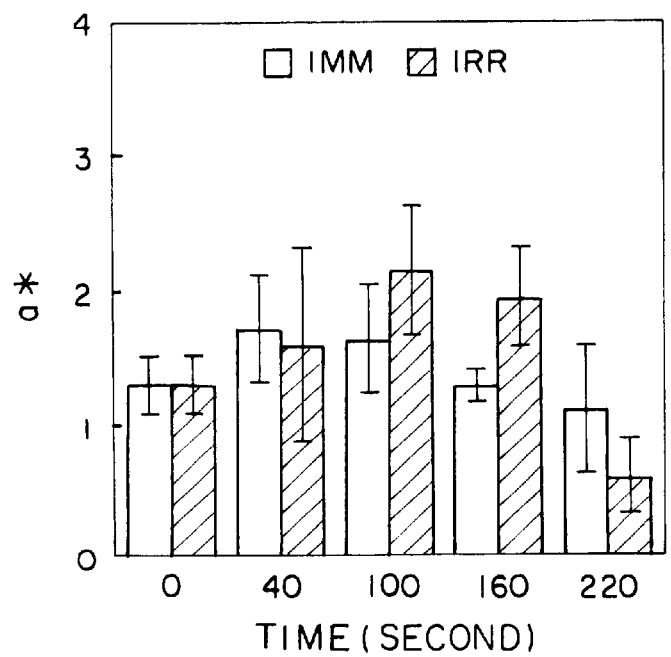
FIG. 5 is a graph showing the relationship between the change in the a* color system of the oxide film illustrated in FIG. 2 and the irradiation time of the visible ray.
Figure 6:
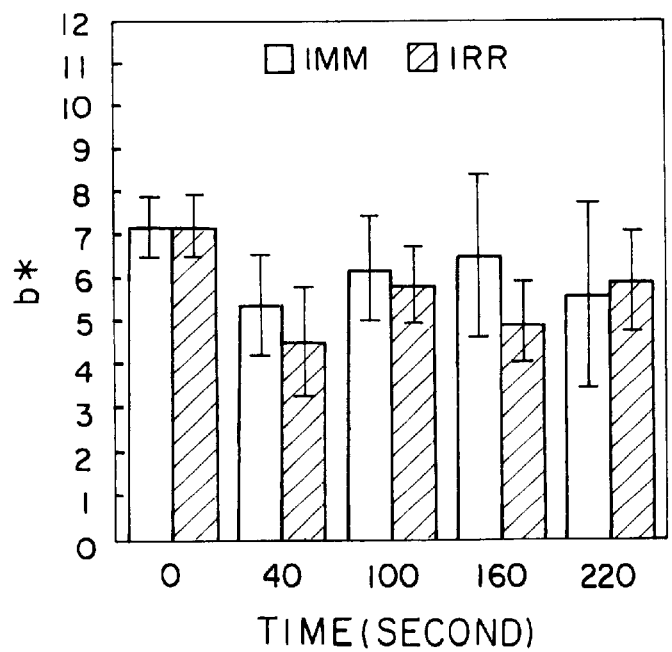
FIG. 6 is a graph showing the relationship between the change in the b* color system of the oxide film illustrated in FIG. 2 and the irradiation time of the visible ray.

FIGS. 4, 5, and 6 show the relationship between the change in the L* a* b* color systems and the irradiation time of the visible ray as the light beam 15. In these figures, IMM represents samples (hereinafter will be referred to as "dipped samples") in which the titanium plate was dipped in the hydrogen peroxide solution 13 without irradiation and IRR represents samples (hereinafter will be referred to as "irradiated samples") in which the hydrogen peroxide solution was dropped onto the titanium plate and the visible ray was irradiated towards the titanium plate.

FIG. 4 shows the change in the L* color system (lightness). In the irradiated samples, the L* color system representative of the lightness is not substantially changed.

FIG. 5 shows the change in the a* color system (redness-greenness). In the irradiated samples, the a* color system exhibits a greatest level when the irradiation is carried out for 100 seconds. The titanium plate is increased in yellowish.

FIG. 6 shows the change in the b* color system (yellowness-blueness). In the b* color system, no difference was observed between the dipped samples and the irradiated samples.

Figure 7:
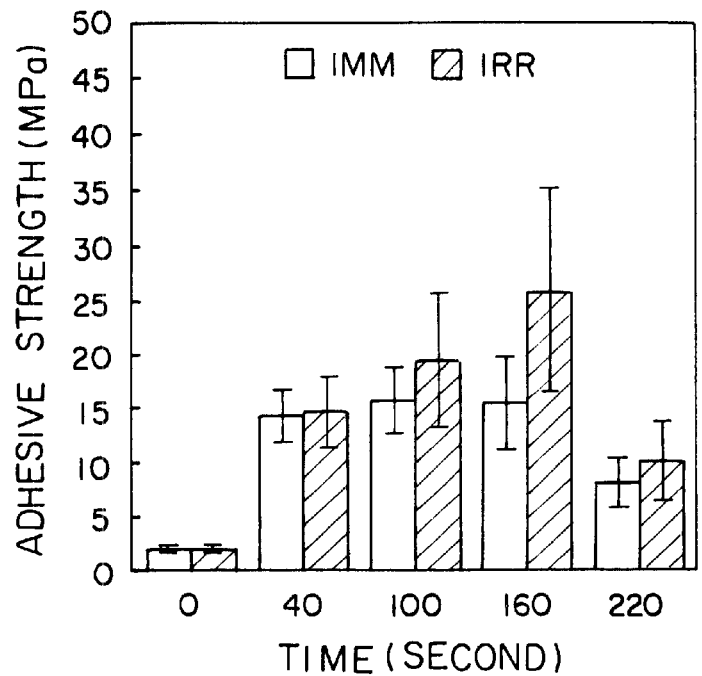
FIG. 7 is a graph showing the result of measurement of the adhesive strength between the metallic member and the object illustrated in FIG. 3 in terms of shear bond strength.

Referring to FIG. 7, the titanium plate was used as the metallic member 11 and the hydrogen peroxide solution 13 was dropped onto the titanium plate. The visible ray was irradiated towards the titanium plate for 40 seconds, 100 seconds, 160 seconds, and 200 seconds to perform surface treatment. Thereafter, the adhesive 19 was adhered to the surface of the titanium plate. The adhesive strength (MPa) was measured as shear bond strength.

The irradiated sample in which the irradiation was carried out for 40 seconds is not different in adhesive strength from the dipped sample. Those samples in which the irradiation was carried out for 100 seconds and 160 seconds exhibited greater adhesive strength as compared with the dipped samples.

Figure 8:
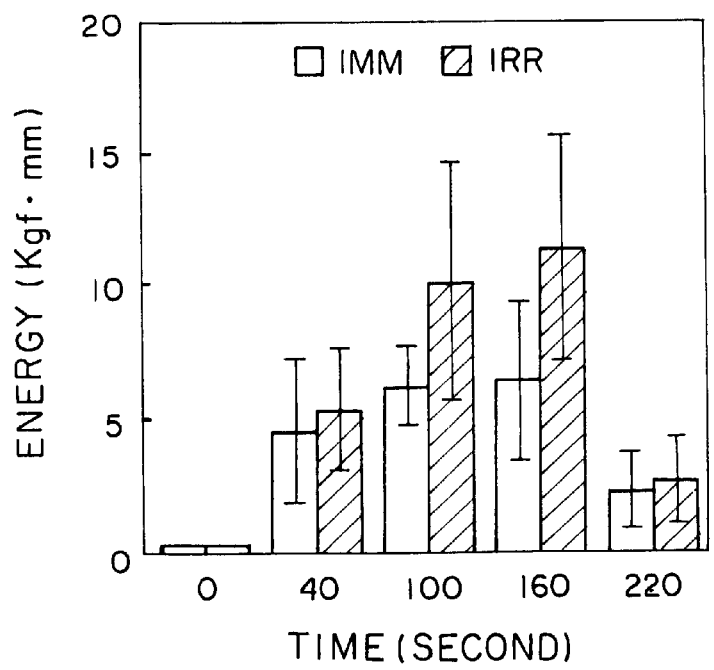
FIG. 8 is a graph showing the result of measurement of the energy consumption before breakage of adhesion between the metallic member and the object illustrated in FIG. 3.

FIG. 8 shows the energy consumed before breakage of the adhesive 19. As seen from FIG. 8, the irradiated samples required greater energy as compared with the dipped samples when the oxidization was carried out for 100 seconds and 160 seconds.

Figure 9:
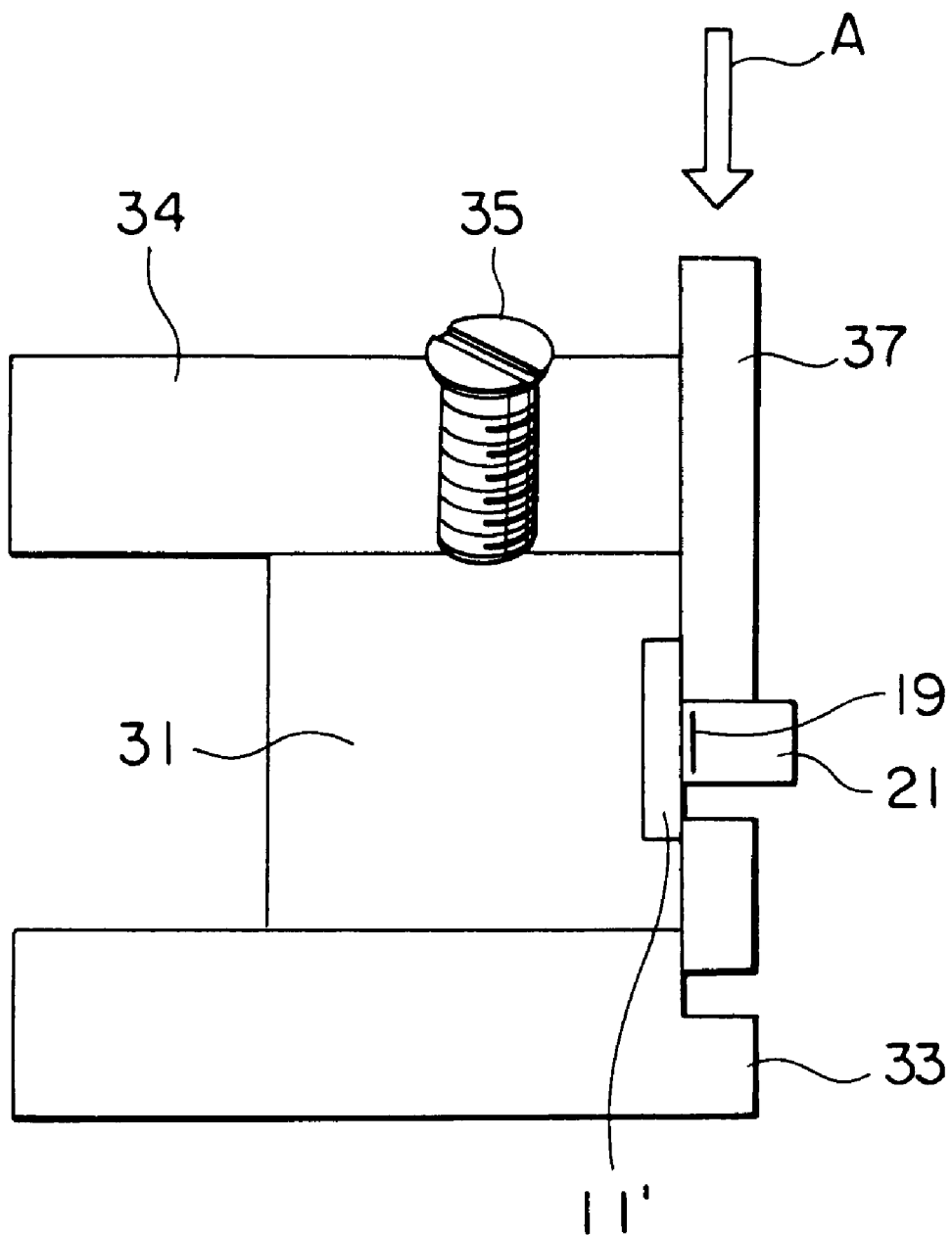
FIG. 9 is a sectional view for describing the method of measurement of the adhesive strength.

Referring to FIG. 9, measurement of the adhesive strength was carried out in the following manner. A titanium plate 11' as the metallic member 11 was integrally fixed by molding to a block 31 made of epoxy resin with one surface of the titanium plate 11' exposed. The object 21 made of metal was fixed through the adhesive 19 to the one surface of the titanium plate 11'. The block 31 was fixed through a screw 35 to stainless steel bases 33 and 34. Thereafter, the object 21 is applied with a load by a pressing member 37 in a direction depicted by an arrow A in the figure. Thus, the adhesive strength (MPa) was measured as the shear bond strength.

Figure 10:
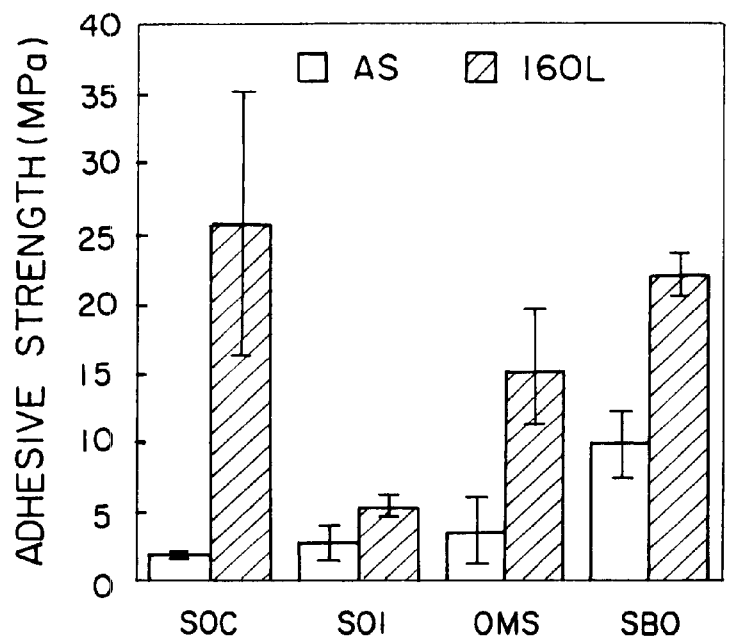
FIG. 10 is a graph showing the result of measurement of the adhesive strength after a titanium plate is adhered by the use of various kinds of adhesives.

Referring to FIG. 10, measurement of the adhesive strength was carried out with respect to various kinds of adhesives. After the hydrogen peroxide solution 13 was dropped onto the titanium plate 11', the titanium plate 11' was irradiated for 160 seconds and oxidized. By the use of different kinds of adhesives 19, the titanium plate 11' was cemented. Thereafter, the adhesive strength (MPa) was measured. For all of the adhesives 19, the adhesive strength was great as compared with untreated samples without irradiation. In the figure, AS represents the untreated samples without irradiation while 160L represents irradiated samples irradiated by the visible ray for 160 seconds. Thus, it has been revealed that the method is effective.

Figure 11:
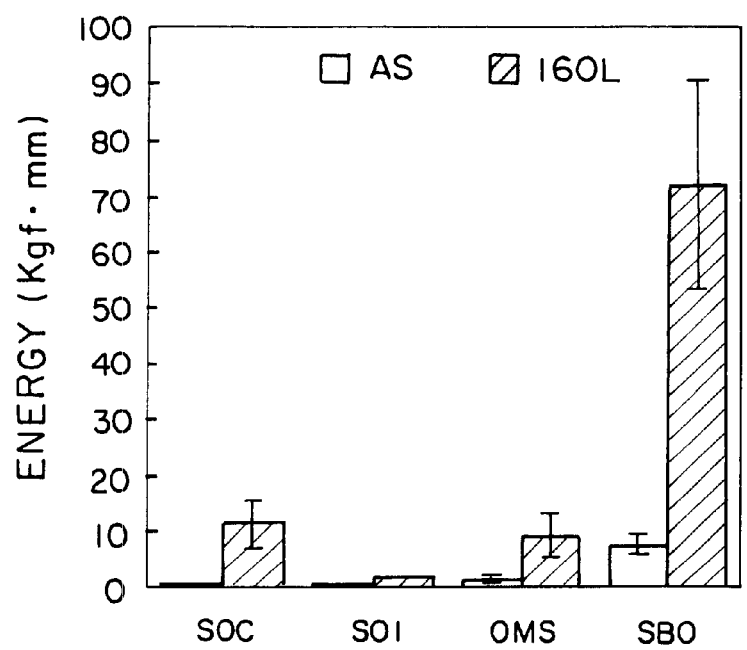
FIG. 11 is a graph showing energy consumption before separation of the object from the titanium plate.

FIG. 11 shows the energy (Kgf·mm) consumed before the object 21 is sheared off from the titanium plate 11' illustrated in FIG. 9. As seen from the figure, greater energy was consumed as a result of irradiation treatment.

In FIGS. 10 and 11, the trade name of the adhesives 19 used herein are as follows:

SOC: Sealant (manufactured by Shofu Dental)

SOI: Imperva (manufactured by Shofu Dental)

OMS: OrthoSolo (manufactured by Ormco, a subsidiary of Sybron Dental Specialties)

SBO: Super Bond (manufactured by Sun Medical)

As a source of the visible ray, use is made of a halogen lamp. As a source of the laser beam, use is made of an argon gas laser, an erbium laser, a $CO_2$ laser, a He-Ne laser, a YAG (Nd:YAG) laser, a GaAlAs laser, and so on. By irradiation of the visible ray, the laser beam, or the ultraviolet ray, hydro radicals are produced to oxidize the surface of the metallic member 11.

As the hydrogen peroxide solution 13, use may be made of 34% hydrogen peroxide solution generally available. The hydrogen peroxide solution 13 is diluted to 60% or 80% before it is applied to the surface of the metallic member 11.

In case where a titanium implant treated by applying the hydrogen peroxide solution 13 and irradiating the visible ray, the laser beam, or the ultraviolet ray is used, the bonding strength between the implant and the bone is improved as compared with an implant of unoxidized titanium. Thus, in case where the oxide film 17 is formed, the wettability of the tissue of the bone 31 illustrated in FIG. 3 is also improved.

As described above in conjunction with the embodiment and the specific examples, the method according to this invention comprises the steps of applying the hydrogen peroxide solution onto the surface of the metallic member and irradiating one of the visible ray, the ultraviolet ray, and the laser beam towards the surface of the metallic member through the hydrogen peroxide solution. In this manner, the oxide film equivalent in quality to that obtained by oxidization via heat treatment is formed in a short period on the order of several minutes. Therefore, according to this invention, the oxidization process can be reliably carried out in a short time without heating and oxidizing the metallic member in the electric furnace.

Since the metallic member need not be heated and oxidized in the electric furnace, the whole process from the oxidization to the adhesion is reliably carried out in a short time.

In addition, by the use of the method according to this invention, it is possible to avoid deterioration in quality of the metallic member as a result of formation of the oxide film at high temperature and to consume a long time for polishing the surface of the metallic member.

What is claimed is:

1. A method of forming an oxide film on a metallic member, the method comprising the steps of:

selectively applying a hydrogen peroxide solution onto the metallic member to oxidize the metallic member and to form the oxide film; and irradiating a light beam onto the surface of the metallic member through the hydrogen peroxide solution to promote oxidization of the surface of the metallic member, the light beam being one of a visible ray, a laser beam, or an ultraviolet ray.

2. A method as claimed in claim 1, wherein the metallic member is made of a material selected from a group consisting of a cobalt-chromium alloy, a nickel-chromium alloy, a stainless steel, pure titanium, a titanium alloy, a platinum gold alloy, a gold-silver-palladium alloy, a silver alloy, and a gold alloy.

3. A method as claimed in claim 1, wherein the metallic member is an implant to be implanted in a living bone.

4. A method as claimed in claim 3, wherein the metallic member is made of a material selected from a group consisting of a cobalt-chromium alloy, a nickel-chromium alloy, a stainless steel, pure titanium, a titanium alloy, a platinum gold alloy, a gold-silver-palladium alloy, silver alloy, and a gold alloy.

5. A method as claimed in claim 3, wherein the light beam is a visible ray.

6. A method as claimed in claim 3, wherein the light beam is a laser beam.

7. A method as claimed in claim 3, wherein the light beam is an ultraviolet ray.

8. A method as claimed in claim 3, wherein the metallic member is made of a cobalt-chromium alloy.

9. A method as claimed in claim 3, wherein the metallic member is made of a nickel-chromium alloy.

10. A method as claimed in claim 3, wherein the metallic member is made of stainless steel.

11. A method as claimed in claim 3, wherein the metallic member is made of pure titanium.

12. A method as claimed in claim 3, wherein the metallic member is made of a titanium alloy.

13. A method as claimed in claim 3, wherein the metallic member is made of a platinum gold alloy.

14. A method as claimed in claim 3, wherein the metallic member is made of a gold-silver-palladium alloy.

15. A method as claimed in claim 3, wherein the metallic member is made of a silver alloy.

16. A method as claimed in claim 3, wherein the metallic member is made of a gold alloy.

17. A method as claimed in claim 1, further comprising fixing the metallic member by an adhesive to one of an orthodontic bracket, a crown, a dental bridge, or an inlay for dental conservative restoration.

18. A method as claimed in claim 4, further comprising fixing the metallic member by an adhesive to one of an orthodontic bracket, a crown, a dental bridge, or an inlay for dental conservative restoration.

* * * * *